United States Patent [19]

Meyer et al.

[11] 4,387,251
[45] Jun. 7, 1983

[54] PROCESS FOR THE PREPARATION OF PURE 4,4'-DIHYDROXYPHENYL ALKANES OR 4,4'-DIHYDROXYDIPHENYL CYCLOALKANES

[75] Inventors: Karl-Heinrich Meyer; Ludwig Bottenbruch, both of Krefeld; Wolfgang Jakob, Moers, all of Fed. Rep. of Germany

[73] Assignee: Bayer Aktiengesellschaft, Leverkusen, Fed. Rep. of Germany

[21] Appl. No.: 285,046

[22] Filed: Jul. 20, 1981

Related U.S. Application Data

[63] Continuation of Ser. No. 182,106, Aug. 28, 1980, abandoned.

[30] Foreign Application Priority Data

Aug. 31, 1979 [DE]  Fed. Rep. of Germany ....... 2935316

[51] Int. Cl.³ .............................................. C07C 39/16
[52] U.S. Cl. .................................... 568/727; 568/728
[58] Field of Search ................ 568/722, 727, 728, 723

[56] References Cited

U.S. PATENT DOCUMENTS

| | | | |
|---|---|---|---|
| 2,468,982 | 5/1949 | Jansen | 568/728 |
| 2,542,688 | 2/1951 | Johnson et al. | 568/727 |
| 2,775,620 | 12/1956 | Williamson | 568/728 |
| 2,807,653 | 9/1957 | Filbey | 568/727 |
| 2,923,744 | 2/1960 | Scriabine et al. | 568/728 |
| 3,207,794 | 9/1965 | Haines et al. | 568/728 |
| 3,919,052 | 3/1982 | Styskin et al. | 568/728 |
| 3,919,053 | 3/1982 | Heuser et al. | 568/727 |
| 3,920,573 | 11/1975 | Vegter et al. | 568/728 |

FOREIGN PATENT DOCUMENTS 641014  5/1962  Canada .............................. 568/728

*Primary Examiner*—Werren B. Lone
*Attorney, Agent, or Firm*—Connolly and Hutz

[57] ABSTRACT

A process for the preparation of bisphenols, which comprises condensing an aliphatic or cycloaliphatic ketone with a phenol having a free p-position in the presence, as a condensing agent, of from 0.3 to 3 mols, per mol of ketone, of an aromatic sulphonic acid of the formula (III) or (IV):

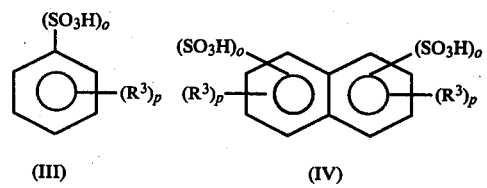

(III)              (IV)

wherein
$R^3$ is an inert organic radical,
o represents an integer from 1 to 4, and
p represents 0 or an integer from 1 to 4, and in the presence of an organic solvent, in which the aromatic sulphonic acid is effectively soluble and the bisphenol or the phenol adduct which is produced is as slightly soluble as possible, the reaction being carried out at a temperature at which the produced diphenol crystallises as extensively as possible as such or as a phenol adduct during or at the end of the reaction; isolating the crystalline separated bisphenol or its adduct; and removing the adhering phenol or solvent.

4 Claims, No Drawings

PROCESS FOR THE PREPARATION OF PURE 4,4'-DIHYDROXYPHENYL ALKANES OR 4,4'-DIHYDROXYDIPHENYL CYCLOALKANES

CROSS REFERENCE TO RELATED APPLICATION

This application is a continuation of application Ser. No. 182,106 filed Aug. 28, 1980, and now abandoned.

This invention relates to a particularly simple process for the preparation of 4,4'-dihydroxydiphenyl alkanes or -cycloalkanes (bisphenols) in a purity such that they can be used directly for the production of high-grade plastics materials.

Hitherto, the only technically significant method for the preparation of bisphenol A (2,2-bis(4-hydroxyphenyl)propane) has been the reaction of acetone with excess phenol in the presence of an acidic condensing agent. The reaction can be catalysed by mercapto compounds. Strong acids such as sulphuric acid or hydrochloric acid are initially used as an acidic condensing agent, but they have to be removed completely from the reaction mixture because of their severe corrosive action and thermal impairment of the product. Nowadays, anhydrous insoluble cation exchange resins containing sulphonic acid groups are mainly used as the acidic condensing agent because they can be completely separated from the liquid reaction mixture. For the reaction, a liquid mixture of acetone and phenol is passed through the solid ion exchanger and the bisphenol formed, which has been dissolved therein, is isolated (cf. German Auslegeschrift No. 1,186,834).

In all these processes for the preparation of bisphenol A, undesired by-products are procued, particularly o,p-bisphenol, other condensates such as trisphenol, chromans, indans and higher condensed darkly coloured resins. After 6 hours at 70° C., reaction products having approximately the following composition are, for example, formed in the exchanger bed:

| | |
|---|---|
| Bisphenol A (p,p-compound) | 76.2% |
| By-products: | |
| o,p-bisphenol | 12.8% |
| Indan and spiroindan compounds | 4.1% |
| Chromans | 1.6% |
| Trisphenol | 1.3% |
| Others | 4.0% |

The by-products, particularly those which are mono- and trifunctional and discolouring, have to be removed before the conversion into plastics materials, e.g. polycarbonates, for example by crystallising bisphenol-phenol-adducts from a phenolic solution. In this case, the by-products remain in the mother liquor and can either be thermally dissociated back into phenol and acetone in an alkaline-aqueous solution or can be recycled for partial rearrangement into the p,p-bisphenol in the reaction process.

Other purification processes are based on recrystallisation or extraction using different solvents, or high-vacuum distillation, but all of these processes are very complex.

Fewer by-products are produced when the initially liquid reaction mixture is allowed to crystallise as extensively as possible in the ion exchanger bed. However, it is then difficult to separate the crystals and the exchanger resin from each other without damaging them.

The present invention provides a process for the preparation of bisphenols by condensing aliphatic or cycloaliphatic ketones with phenols having a free p-position in the presence of aromatic sulphonic acids as the condensing agent and a solvent, which is characterised by the following measures:

(1) the use of an organic solvent, in which the aromatic sulphonic acids are readily soluble and the bisphenol which is formed or its phenol adduct is as slightly soluble as possible;

(2) the use of from 0.3 to 3 mols per mol of ketone of an aromatic sulphonic acid of the formulae (III) and (IV):

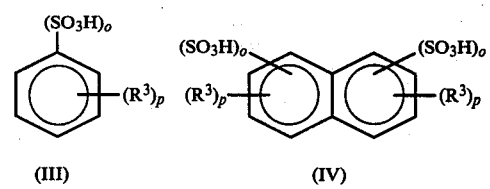

wherein
$R^3$ is an inert organic radical,
o represents an integer from 1 to 4, and
p represents an integer from 0 to 4;

(3) the reaction is carried out at a temperature at which the bisphenol which has been produced crystallises as extensively as possible as such or as a phenol adduct during or at the end of the reaction;

(4) isolating the crystalline separated bisphenol or its adduct; and (5) removing the adhering phenol or solvent.

The bisphenol which has been obtained in this manner has a surprisingly high purity and can be used directly for the preparation of polycarbonate resins or triazine resins.

The sulphonic acids used according to the invention do indeed bind considerable quantities of water, but their efficiency as a condensing agent decreases with an increasing content of water. Therefore, the sulphonic acids have to be greatly concentrated or large quantities of the acid have to be used. It is particularly favourable to continuously distill off the reaction water—one mol per mol of bisphenol. This is particularly recommended when the process is carried out in a continuous manner. In order to distill off the water, conventional methods of vacuum distillation or azeotropic distillation of solvent-water mixtures can be applied.

In the continuous embodiment of the process, the liquid reaction mixture consisting of the solvent, sulphonic acid, excess phenol and smaller quantities of dissolved reaction products is circulated, phenol and ketone being continuously supplied to the circuit and the pure crystalline reaction product and the reaction water are removed from the circuit.

The process of the invention is suited preferably for the preparation of bisphenol A. However, other very different bisphenols can also be prepared. Aliphatic and cycloaliphatic ketones of the formula (I):

wherein
R and $R^1$ are the same or different and represent a $C_1$-$C_{10}$ alkyl radical or a $C_6$-$C_8$ cycloalkyl radical, can be preferably used as starting compounds. Ketones are particularly suitable, such as acetone, methyl ethyl ketone, methyl-n-propyl ketone and cyclohexanone.

Compounds of the general formula (II) are preferably used as phenols having a free p-position:

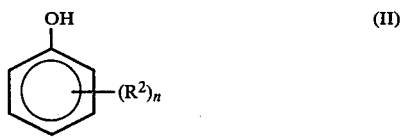

(II)

wherein:
$R^2$ represents a $C_1-C_8$-alkyl radical, preferably methyl-, tertiary-butyl- or isopropyl-, and
n represents 0 or an integer from 1 to 4.

In this process, the phenols are constantly used in excess quantities, preferably between 3 and 15 mols of phenol per mol of ketone.

All water-binding aromatic sulphonic acids which dissolve in organic solvents are particularly suitable as acidic condensing agents. All mono- and polysulphonic acids of the general formulae (III) and (IV) are preferred:

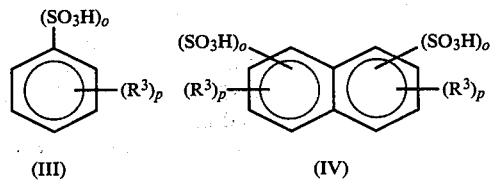

(III)           (IV)

wherein
$R^3$ is an inert organic radical,
o represents an integer from 1 to 4, and
p represents an integer from 0 to 4

$R^3$ is preferably a $C_1-C_{12}$ aliphatic radical, a cycloaliphatic or aliphatic-aromatic radical, or Cl, Br, OH, SH, $OR^4$, $SR^4$, $SO_2R^4$, $NO_2$, COOH, and $R^4$ is an aliphatic or aromatic hydrocarbon radical which can carry inert substituents. Phenol sulphonic acid is particularly preferred.

It is possible to use these sulphonic acids in broad ranges as condensing agents for the preparation of bisphenol, but they are preferably used in quantities of between 0.3 and 3 mols per mol of the ketone which is used.

The rate of the reaction can be accelerated by adding conventional catalysts containing sulphur. It is also dependent on the type and quantity of the sulphonic acid and also on the temperature of the reaction. However, as has already been mentioned, the content of water of the condensing agent has a particular effect on the rate of the reaction. It is therefore appropriate to dry the sulphonic acid intensively before it is used, e.g. for 3 hours under a vacuum of 20 mbar at from 80° to 100° C.

The solvent or solvent mixture which has been selected for the process has to maintain the sulphonic acid, which is used as the condensing agent, completely in solution and must simultaneously effect the separation of the bisphenol or its phenol-adduct which has formed in an effectively filterable form which is as pure as possible. For this purpose, many aliphatic, cycloaliphatic and aromatic hydrocarbons and halogen-hydrocarbons are suitable such as ligroin, cyclohexane, benzene, toluene, xylene, chlorobenzene, o-dichlorobenzene, methylene chloride and 1,2-dichloroethane, and also various other compounds, provided they are poor solvents for bisphenols and/or their adducts, but effective solvents for sulphonic acids. Those phenols which are used for the preparation of bisphenols are particularly suitable for this purpose if they are used in sufficient excess.

EXAMPLE 1

In order to examine the influence which the quantity of the acidic condensing agent has on the yield and purity of the bisphenol which has formed, different quantities of freshly distilled benzene-sulphonic acid ($Bp_{0.2}$ from 142° to 144° C.) in parallel mixtures, were respectively dissolved homogeneously in a mixture of 180 g of phenol, 30 g of acetone, 100 g of toluene and 0.4 g of β-mercaptopropionic acid in a 500 ccm-stirrer-equipped flask at 45° C. and were maintained at this temperature for 6 hours with stirring.

The yield of crystals which formed was then filtered over a suction filter and the crystals were washed with the same quantity of toluene, by using the washing liquid in several portions and thereby adding that quantity of phenol which was removed from the reaction mixture by the separated crystals in reacted and adhering form. Adhering acid was thereby completely removed from the colourless crystals. The reaction product in the crystals and its content of p,p-bisphenol A (p,p-BPA) were determined by means of gas-chromatographic analysis.

The proportion of the reaction product dissolved in the mother liquor was also examined by means of gas-chromatography, after it had been obtained as a residue from the organic solution by neutralisation and washing out the sulphonic acid with water and subsequently distilling off the solvent and also the unreacted phenol and acetone.

The results summarised in the following table show that when greater quantities of sulphonic acid are used, the crystal yield greatly increases with a constant outstanding quality of bisphenol A, while the proportion of bisphenol remaining dissolved in the liquid reaction phase is practically unchanged in nature and quantity.

TABLE 1

| Mixture No. | 1 | 2 | 3 | 4 |
|---|---|---|---|---|
| Benzene sulphonic acid which was used | 1 g | 5 g | 10 g | 20 g |
| Time until the start of crystallisation | 230 Min | 165 Min | 100 Min | 40 Min |
| Quantity of crystals after washing | 16.4 g | 52.2 g | 91.9 g | 116.2 g |
| Quantity of condensation product in the crystals | 7.77 g | 24.71 g | 43.26 g | 59.58 g |
| Content therein of p,p-BPA | 99.93% | 99.92% | 99.97% | 99.95% |
| Residue from mother liquor | 16.32 g | 14.69 g | 17.61 g | 15.74 g |
| Content therein of p,p-BPA | 92.43% | 91.36% | 94.76% | 93.88% |
| Conversion based on the acetone which | 20.43% | 33.42% | 52.64% | 63.89% |

TABLE 1-continued

| Mixture No. | 1 | 2 | 3 | 4 |
|---|---|---|---|---|
| was used | | | | |

EXAMPLE 2

In the following series of experiments, various sulphonic acids were used together with different solvents.

(a) A solution of 200 g of phenol, 100 g of light petrol (bp from 90° to 100° C.), 10 g of dodecylbenzene sulphonic acid (trade name Marlon AS 3) and 0.2 g of β-mercaptopropionic acid was brought to boiling point with distillation and reflux by applying a diminished pressure at 45° C. in a stirrer-equipped apparatus with a water separator. Thereby, 20 g of acetone were introduced over 5 hours and the reaction water which was produced was separated from the distillate. The crystals formed were then filtered off and washed with light petrol and phenol (as in Example 1).

The mother liquor was then reacted with 20 g of acetone again at 45° C. for 5 hours as described above. After separating the freshly formed crystals, the mother liquor was again reacted with 20 g of acetone and the reaction mixture was again separated. The gas-chromatographic analysis of the products which were worked up produced the following results:

| | |
|---|---|
| 1. Crystallised material content of BPA | 27.82 g therein 99.91% p,p-BPA |
| 2. Crystallised material content of BPA | 37.64 g therein 98.88% p,p-BPA |
| 3. Crystallised material content of BPA | 37.86 g therein 99.89% p,p-BPA |
| Residue of the remaining mother liquor | 27.63 g therein 90.12% p,p-BPA |

(b) A solution consisting of 282 g of phenol, 22.9 g of acetone, 65 g of 1,2-dichloroethane, 65 g of p-toluene sulphonic acid (content of water 10%) and 0.8 g of β-mercaptopropionic acid was stirred for 3 hours at 45° C. The crystals which were produced were then sucked off and washed free from acid with solvent and phenol (as in Example 1).

The mother liquor was then freed from the reaction water by means of reflux distillation under vacuum using a water separator, and the mother liquor was again reacted with 22.9 g of acetone. The entire process was repeated and the crystals and the residue of the remaining mother liquor were then analysed.

| | |
|---|---|
| 1. Crystallised material content of BPA | 43.57 g therein 99.87% p,p-BPA |
| 2. Crystallised material content of BPA | 87.13 g therein 99.42% p,p-BPA |
| 3. Crystallised material content of BPA | 88.80 g therein 99.89% p,p-BPA |
| Residue of the mother liquor | 45.53 g therein 92.01% p,p-BPA |

EXAMPLE 3

The following other bisphenols were synthesised in a manner similar to that of the previous Examples and the conversion and purity of the crystalline reaction product were thereby determined.

(a) 188 g of phenol, 49.1 g of cyclohexane, 10 g of benzene sulphonic acid, 100 g of toluene, 0.3 g of β-mercaptopropionic acid, reaction time 24 hours, conversion 79%, content of p,p-bisphenol in the crystalline reaction product: 99.65% of 4,4'-dihydroxydiphenyl cyclohexane-1,1.

(b) 188 g of phenol, 36 g of methylethyl ketone, 20 g of naphthalene-1-sulphonic acid-4(content of water 1%), 0.3 g of β-mercaptopropionic acid, no additional solvent, reaction time of 24 hours, conversion 73.5%; content of p,p-bisphenol in the crystalline reaction product 99.12%.

(c) 235 g of 2,6-dimethylphenol, 30 g of acetone, 36 g of p-phenylsulphonic acid (dried for 3 hours at 80° C. and 20 mbar), 0.3 g of β-mercaptopropionic acid, no additional solvent, reaction time of 2 hours, conversion 51.3%, content of p,p-bisphenol in the crystalline reaction product: 99.31% 4,4'-dihydroxy-2,6-dimethyldiphenyl propane-2,2.

EXAMPLE 4

For a series of experiments, re-using the mother liquor 30 times, a solution of 310 g of phenol 26 g of acetone, 49 g of p-phenol sulphonic acid (freshly dried) and 0.4 g of β-mercaptopropionic acid was stirred for 3 hours at 45° C. The crystals were then separated and were washed free from acid with the corresponding quantity of phenol (as in Example 1) in several portions. The mother liquor and washing liquid were then distilled for one hour at 7 mbar and at 50° C. in order to remove the reaction water and were then reacted again with 26 g of acetone as described above. This operation was repeated to the 30th mixture and then the crystals and the residue of the remaining mother liquor were analysed.

All 30 crystal samples had a p,p'-BPA content of above 99.95%, in some cases at 100%, while the remaining residue of mother liquor still contained 90.01% of p,p'-BPA. The average conversion per sample was 52% based on the acetone which was used. The proportion of p,p'-BPA was 99.49% based on the total reaction product including the residue of mother liquor.

A larger quantity of bisphenol A, prepared from the obtained crystalline adducts by distilling off the phenol, was examined in the following manner for its suitability for the preparation of polycarbonate: 91 g of the bisphenol were dissolved in 500 g of a 6.5% aqueous soda lye and were stirred together with 900 g of methylene chloride and 2 g of p-tertiary butyl phenol at 25° C. 51.4 g of gaseous phosgene were introduced into this mixture over 30 minutes and the pH-value of the mixture was held at between 13.0 and 13.5 by careful further addition of a little 6.5% soda lye. 8 ccm of a 4% aqueous triethyl amine solution were then added, followed by stirring for a further 45 minutes. The lower organic phase was then separated off and washed several times with distilled water. The polycarbonate which was produced was then isolated in a conventional manner by distilling off the solvent, whereby a very light and clear product having a relative viscosity (0.5% in methylene chloride) of 1.30 was obtained, which is characteristic of a high-molecular-weight, good quality polycarbonate.

We claim:

1. A process for the preparation of bisphenols which comprises condensing an aliphatic or cycloaliphatic ketone with a phenol having a free p-position at a temperature of 45° C., the molar ratio of phenol to ketone during said condensation being between 3 and 15 moles of phenol per mol of ketone, in the presence, as a condensing agent, of from 0.3 to 3 moles, per mol of ketone, of an aromatic sulphonic acid of the formula

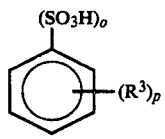

or of the formula

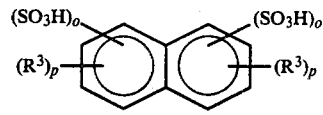

wherein $R^3$ is an inert organic radical, o is an integer of from 1 to 4 and p is 0 or an integer of from 1 to 4, and in the presence of an organic solvent in which the aromatic sulphonic acid is effectively soluble and in which the bisphenol or the phenol adduct which is produced is as slightly soluble as possible, isolating the crystalline separated bisphenol or its adduct, and removing the adhering phenol or solvent.

2. A continuous process according to claim 1, wherein the reaction mixture is circulated, bisphenol and water being continuously removed and phenol and ketone being continuously added.

3. A process according to claim 1 or 2, in which the water produced in the reaction is removed by utilizing the heat from the crystallization process.

4. A process according to claim 1, in which the phenol itself is used as a solvent.

* * * * *